(12) United States Patent
Won et al.

(10) Patent No.: US 12,295,967 B2
(45) Date of Patent: May 13, 2025

(54) PHARMACEUTICAL COMPOSITION FOR PREVENTION OR TREATMENT OF FLAVIVIRUS INFECTION

(71) Applicants: LEMONEX INC., Seoul (KR); SEOUL NATIONAL UNIVERSITY R&DB FOUNDATION, Seoul (KR)

(72) Inventors: Cheol Hee Won, Seoul (KR); Dal Hee Min, Seoul (KR)

(73) Assignees: LEMONEX INC., Seoul (KR); SEOUL NATIONAL UNIVERSITY R & DB FOUNDATION, Seoul (KR)

( * ) Notice: Subject to any disclaimer, the term of this patent is extended or adjusted under 35 U.S.C. 154(b) by 804 days.

(21) Appl. No.: 17/051,117

(22) PCT Filed: Apr. 24, 2019

(86) PCT No.: PCT/KR2019/004974
§ 371 (c)(1),
(2) Date: Oct. 27, 2020

(87) PCT Pub. No.: WO2019/209035
PCT Pub. Date: Oct. 31, 2019

(65) Prior Publication Data
US 2021/0228607 A1 Jul. 29, 2021

Related U.S. Application Data (60) Provisional application No. 62/663,312, filed on Apr. 27, 2018.

(30) Foreign Application Priority Data

Apr. 24, 2019 (KR) .................. 10-2019-0048075

(51) Int. Cl.
| | |
|---|---|
| *A61K 31/7036* | (2006.01) |
| *A61K 31/282* | (2006.01) |
| *A61K 31/47* | (2006.01) |
| *A61K 31/4706* | (2006.01) |
| *A61K 31/496* | (2006.01) |
| *A61K 31/536* | (2006.01) |
| *A61K 31/5415* | (2006.01) |
| *A61K 31/546* | (2006.01) |
| *A61K 31/661* | (2006.01) |
| *A61K 31/7048* | (2006.01) |
| *A61K 38/12* | (2006.01) |
| *A61K 38/14* | (2006.01) |
| *A61P 31/14* | (2006.01) |

(52) U.S. Cl.
CPC ........ *A61K 31/7036* (2013.01); *A61K 31/282* (2013.01); *A61K 31/47* (2013.01); *A61K 31/4706* (2013.01); *A61K 31/496* (2013.01); *A61K 31/536* (2013.01); *A61K 31/5415* (2013.01); *A61K 31/546* (2013.01); *A61K 31/661* (2013.01); *A61K 31/7048* (2013.01); *A61K 38/12* (2013.01); *A61K 38/14* (2013.01); *A61P 31/14* (2018.01); *C12Y 203/01059* (2013.01)

(58) Field of Classification Search
CPC .. A61K 31/7036; A61K 31/282; A61K 31/47; A61K 31/4706; A61K 31/496; A61K 31/536; A61K 31/5415; A61K 31/546; A61K 31/661; A61K 31/7048; A61K 38/12; A61K 38/14; A61P 31/14; C12Y 203/01059
See application file for complete search history.

(56) References Cited

U.S. PATENT DOCUMENTS

| | | | |
|---|---|---|---|
| 9,730,921 B2 | 8/2017 | Abraham et al. | |
| 2009/0227637 A1* | 9/2009 | Weber | ..... A61P 31/12 514/350 |
| 2011/0183892 A1 | 7/2011 | Dinman et al. | |
| 2017/0173001 A1* | 6/2017 | May | ..... A61P 25/00 |

FOREIGN PATENT DOCUMENTS

| | | | |
|---|---|---|---|
| CN | 106983750 A | 7/2017 | |
| KR | 10-20170105113 A | 9/2017 | |
| MX | 2011004158 A1 * | 10/2012 | |
| MX | 2015013285 A | 3/2017 | |
| RU | 2547835 C1 * | 4/2015 | |
| WO | WO-2004067567 A2 * | 8/2004 | ......... C07K 16/1081 |
| WO | WO-2015051281 A1 * | 4/2015 | .......... A61K 31/496 |
| WO | 2016-044095 A1 | 3/2016 | |
| WO | 2017-181098 A2 | 10/2017 | |
| WO | WO-2018119371 A1 * | 6/2018 | .......... A61K 31/427 |

OTHER PUBLICATIONS

Wang et al ("Hhydroxychloroquine-Inhibited Dengue Virus is Associated with Host Defense Machinery", Journal of Interferon & Cytokine Research, vol. 35, No. 3, Mar. 3, 2015) (Year: 2015).*

(Continued)

*Primary Examiner* — Eric Olson
*Assistant Examiner* — Benjamin M Brandsen
(74) *Attorney, Agent, or Firm* — The PL Law Group, PLLC (57) ABSTRACT

A method for treating a flavivirus infection includes administering to a subject in need thereof a composition which includes at least one of gentamicin sulfate, netilmicin, tobramycin, paromomycin, amikacin, capreomycin, trifluoperazine, dihydrostreptomycin, hydroxychloroquine, thioridazine HCl, efavirenz, miltefosine, nystatin, micafungin, bleomycin, resminostat, montelukast, norfloxacin, nedaplatin and cephalothin, which can exhibit excellent growth inhibition or killing effects of various species of flavivirus genus.

15 Claims, 9 Drawing Sheets
Specification includes a Sequence Listing.

(56) References Cited

OTHER PUBLICATIONS

English language machine translation of MX2015013285A, translated Mar. 15, 2024. (Year: 2017).*
English language machine translation of CN106983750A, translated Mar. 11, 2024. (Year: 2017).*
Espinoza-Gómez, F.; et al. "Dengue Virus Coinfection in Human Immunodeficiency Virus-1-Infected Patients on the West Coast of Mexico" 2017, Am. J. Trop. Med. Hyg., vol. 97, pp. 927-930. (Year: 2017).*
Simanjuntak, Y.; et al. "Repurposing of Prochlorperazine for Use Against Dengue Virus Infection" 2015, The Journal of Infectious Diseases, vol. 211, pp. 394-404. (Year: 2015).*
Chockalingam, K.; et al. "A cell protection screen reveals potent inhibitors of multiple stages of the hepatitis C virus life cycle" 2010, Proceedings of the National Academy of Sciences, vol. 107, pp. 3764-3769. (Year: 2010).*
English language machine translation of MX 2011004158 A1 (translated Sep. 12, 2024). (Year: 2011).*
Barrows, N. J.; et al. "A Screen of FDA-Approved Drugs for Inhibitors of Zika Virus Infection" 2016, Cell Host and Microbe, vol. 20, pp. 259-270. (Year: 2016).*
Zhang, X. G.; et al. "Antiviral activity of geneticin against dengue virus" 2009, Antiviral Research, vol. 83, pp. 21-27. (Year: 2009).*
English language machine translation of RU 2547835 C1 (translated Sep. 12, 2024). (Year: 2014).*
Te-Wen Chang et al., "In Vitro Biological Activity of Cephalothin", J. Bacteriol., vol. 85, pp. 1022-1027, 1963.
Emilse S. Leal et al., "Discovery of novel dengue virus entry inhibitors via a structure-based approach", Bioorganic & Medicinal Chemistry Letters, vol. 27, pp. 3851-3855, 2017.

International Search Report for PCT/KR2019/004974 mailed on Aug. 19, 2019.
Crystall M. D. Swarbrick et al. "NS3 helicase from dengue virus specifically recognizes viral RNA sequence to ensure optimal replication" 12904-12920 Nucleic Acids Research, 2017, vol. 45, No. 22.
European Search Report For EP19792006.9 issued on Dec. 13, 2021 from European patent office in a counterpart European patent application.
Wang Li-Fong et al., "Hydroxychloroquine-Inhibited Dengue Virus Is Associated with Host Defense Machinery", Journal of Interferon and Cytokine Research., vol. 35, No. 3, Mar. 1, 2015 (Mar. 1, 2015), pp. 143-156, XP055863524.
Carro Ana C et al, "Requirement of cholesterol in the viral envelope for dengue virus infection", Virus Research, Amsterdam, NL, vol. 174, No. 1, Mar. 18, 2013 (Mar. 18, 2013), pp. 78-87, XP028533798.
Cao Bin et al, "Inhibition of autophagy limits vertical transmission of Zika virus in pregnant mice", Journal of Experimental Medicine, vol. 214, No. 8, Aug. 7, 2017 (Aug. 7, 2017), pp. 2303-2313, XP055863527.
Barrows Nicholas J et al, "A Screen of FDA-Approved Drugs for Inhibitors of Zika Virus Infection", Cell Host & Microbe, Elsevier, NL, vol. 20, No. 2, Jul. 28, 2016 (Jul. 28, 2016), pp. 259-270, XP029682741, ISSN: 1931-3128, DOI: 10.1016/J.CHOM.2016.07.004; p. 267; table 2.
E. Mastrangelo et al, "Ivermectin is a potent inhibitor of flavivirus replication specifically targeting NS3 helicase activity: new prospects for an old drug", Journal of Antimicrobial Chemotherapy., vol. 67, No. 8, Apr. 1, 2012 (Aug. 1, 2012), pp. 1884-1894, XP055299519,GB ISSN: 0305-7453, DOI: 10.1093/jac/dks147; p. 1888, col. 1889.
Office action issued on Jan. 16, 2024 from China Patent Office in a counterpart China Patent Application No. 201980028691.7 (English translation is also submitted herewith.).

* cited by examiner

PHARMACEUTICAL COMPOSITION FOR PREVENTION OR TREATMENT OF FLAVIVIRUS INFECTION

CROSS REFERENCE TO RELATED APPLICATIONS AND CLAIM OF PRIORITY

This application claims benefit under 35 U.S.C. 119 (e), 120, 121, or 365(c), and is a National Stage entry from International Application No. PCT/KR2019/004974, filed on Apr. 24, 2019, which claims priority to the benefit of U.S. Provisional Patent Application No. 62/663,312 filed on Apr. 27, 2018 and Korean Patent Application No. 10-2019-0048075 filed in the Korean Intellectual Property Office on Apr. 24, 2019, the entire contents of which are incorporated herein by reference.

TECHNICAL FIELD

The present invention relates to a pharmaceutical composition for preventing or treating flavivirus infection.

BACKGROUND ART

Flaviviruses are small, coated and enveloped positive-strand RNA viruses, some of which may threaten or potentially threaten the health of humans worldwide currently or in the future. For example, yellow fever virus has been a cause of epidemics in certain jungles in sub-Saharan Africa or in parts of South Africa. Many yellow fever infections are not much serious, but they may lead to serious and life-threatening illnesses. Conditions of these diseases have the following two phases. The early acute phase is characterized by high fever, chills, headache, back pain, myalgia, anorexia, nausea and vomiting. After 3 to 4 days, such symptoms disappear. In some patients, these symptoms may recur when the disease enters a so-called virulence phase, that is, "toxic phase." During the toxic phase, high fever reappears and may result in shock, bleeding (e.g., bleeding from the mouth, nose, eyes, and/or stomach), kidney failure and liver failure. In fact, the liver failure is often called "yellow fever" because it causes jaundice, which causes the skin to turn yellow and the eyes become white. Half of patients entering the toxic phase die within 10 to 14 days. However, people who recover from the yellow fever have lifelong immunity to re-infection.

The number of people infected with yellow fever virus has been gradually increased over the past two decades, with about 200,000 cases of yellow fever infections annually, and with about 30,000 deaths annually. Thus, the re-emergence of yellow fever virus poses a serious threat to public health.

Dengue (DEN) viruses are another example of flaviviruses. The dengue virus is transmitted to humans by mosquitoes (mostly *Aedes aegypti*) and causes increasingly serious public health problems worldwide. About 50 out of 100 million people are infected with the dengue virus. In some areas, as much as 63 infection rates have been observed, four antigenic dengue viruses (dengue types 1-4) are spread throughout the Caribbean, Asia and the Americas. DEN infection (dengue hemorrhagic fever/dengue shock syndrome (DHF/DSS)] is an immune-pathological disease that occurs in individuals sequentially infected by DENs of different antigenic types: deaths more than 3.6 million people with dengue hemorrhagic fever (DHF) and 58,000 people with DHF were reported between 1980 and 1995. Because of pathogenic properties of DHF/DSS, it has been considered that optimal dengue vaccines should afford immunity to all four antigen types simultaneously and confer long-lasting immunity. Although active efforts have been made to develop effective dengue vaccines since World War II, there is currently no approved and available dengue vaccine.

Flaviviruses including yellow fever and dengue viruses have two important biological characteristics responsible for induction of disease in humans and animals. One of these two features is nerve tissue affinity, that is, "neurotropism" which refers to a tendency of virus to invade nerve tissues of a host and infect the same. Nerve tissue-friendly (that is, neurotropic) flavivirus infection may cause infection and injury of the brain and spinal cord (i.e., encephalitis), unconsciousness, paralysis, and convulsions. A second feature of the flavivirus infection is visceral organ affinity, i.e., the virus tends to invade and infect vital visceral organs including the liver, kidneys and heart. Visceral organ-friendly flavivirus infections may cause infection and damage to the liver (hepatitis), kidneys (nephritis), and heart muscle (myocarditis), inhibiting these organs from functioning normally. Nerve tissue affinity and visceral organ affinity are considered to be distinct and different features of flavivirus.

Some flaviviruses basically have nerve tissue affinity (e.g. West Nile virus), other some have visceral organ affinity (e.g. yellow fever virus and dengue virus), and the others exhibit both properties. (e.g., Kyasanur Forest Disease Virus). However, both nerve tissue affinity and visceral organ affinity are present more or less in all flaviviruses. Interaction between nerve tissue affinity and visceral organ affinity may occur in the host because the visceral organ is infected prior to attack to the central nervous system. Therefore, nerve tissue affinity depends on the virus's ability to replicate in the extraneural organs (intestines). Such extraneural replication causes viremtia and this viremia may attack the brain and spinal cord.

One attempt to develop a vaccine against flaviviruses was to change virulence properties of the viruses, so that a vaccine virus loses its nerve tissue affinity and visceral organ affinity for humans and animals. In the case of yellow fever virus, two vaccines have been developed: yellow fever 17D and French nerve-tissue affinity vaccine. The yellow fever 17D vaccine was developed by yielding a virus that significantly reduced nerve tissue affinity and visceral organ affinity by serial inoculation, that is, "serial passage" in chicken embryonic tissues. The French nerve-tissue affinity vaccine was developed by serial passage in mouse brain tissues to completely remove visceral organ affinity while remaining nerve tissue affinity. Use of French vaccine has involved a high incidence of nervous system accidents (encephalitis after vaccination). Currently, none of the other viruses is commercially available as an approved vaccine against clinically important flaviviruses with visceral organ affinity such as dengue, West Nile, Omsk Hemorrhagic Fever Virus, etc.

SUMMARY

It is an object of the present invention to provide a composition for preventing or treating flavivirus infections, which is effective to various flaviviruses.

In addition, another object of the present invention is to provide a composition capable of inhibiting growth of various flaviviruses or killing the same.

1. A pharmaceutical composition for preventing or treating flavivirus infection, the composition including: at least one of gentamicin sulfate, netilmicin, tobramycin, paromomycin, amikacin, capreomycin, trifluoperazine, dihydrostreptomycin, hydroxychloroquine, thioridazine HCl, efavirenz, miltefosine, nystatin, micafungin, bleomycin, resminostat, montelukast, norfloxacin, nedaplatin and cephalothin; or at least one of pharmaceutically acceptable salts of the above compounds.

2. The composition according to above 1, wherein the flavivirus infection is an infection derived from Apoi virus, Aroa virus, Bagaza virus, Banzi virus, Bouboui virus, Bukarasa bat virus, Cacipacore virus, Carey Island virus, Cowbone Ridge virus, Dakar bat virus, dengue virus, Edge Hill virus, Entebbe bat virus, Gadgets Gully virus, Ilheus virus, Israel turkey meningoencephalomyelitis virus, Japanese encephalitis virus, Jugra virus, Jutiapa virus, Kadam virus, Kedougou virus, Kokobera virus, Koutango virus, Kyasanur Forest disease virus, Langat virus, Louping ill virus, Meaban virus, Modoc virus, Montana myotis leukoencephalitis virus, Murray Valley encephalitis virus, Ntaya virus, Omsk hemorrhagic fever virus, Phnom Penh bat virus, Powassan virus, Rio Bravo virus, Royal Farm virus, Saboya virus, Saint Louis encephalitis virus, Sal Vieja virus, San Perlita virus, Saumarez Reef virus, Sepik virus, Tembusu virus, Tick-borne encephalitis virus, Tyuleniy virus, Uganda S virus, Usutu virus, Wesselsbron virus, West Nile virus, Yaounde virus, Yellow fever virus, Yokose virus, or Zika Virus.

3. The composition according to above 1, wherein the flavivirus infection is a dengue virus-derived infection.

4. The composition according to above 1, including: at least one of tobramycin, trifluoperazine 2HCl, amikacin hydrate, hydroxychloroquine sulfate, thioridazine HCl, dihydrostreptomycin sulfate, gentamicin sulfate, netilmicin sulfate, capreomycin sulfate, paromomycin sulfate, resminostat, montelukast, norfloxacin, nedaplatin, bleomycin, nystatin, cephalothin, micafungin sodium, efavirenz and miltefosine; or at least one of pharmaceutically acceptable salts of the above compounds.

5. A composition for inhibiting growth of flavivirus or killing the same, the composition including: at least one of gentamicin sulfate, netilmicin, tobramycin, paromomycin, amikacin, capreomycin, trifluoperazine, dihydrostreptomycin, hydroxychloroquine, thioridazine HCl, efavirenz, miltefosine, nystatin, micafungin, bleomycin, resminostat, montelukast, norfloxacin, nedaplatin and cephalothin; or at least one of pharmaceutically acceptable salts of the above compounds.

6. The composition according to above 5, wherein the flavivirus is Apoi virus, Aroa virus, Bagaza virus, Banzi virus, Bouboui virus, Bukarasa bat virus, Cacipacore virus, Carey Island virus, Cowbone Ridge virus, Dakar bat virus, dengue virus, Edge Hill virus, Entebbe bat virus, Gadgets Gully virus, Ilheus virus, Israel turkey meningoencephalomyelitis virus, Japanese encephalitis virus, Jugra virus, Jutiapa virus, Kadam virus, Kedougou virus, Kokobera virus, Koutango virus, Kyasanur Forest disease virus, Langat virus, Louping ill virus, Meaban virus, Modoc virus, Montana myotis leukoencephalitis virus, Murray Valley encephalitis virus, Ntaya virus, Omsk hemorrhagic fever virus, Phnom Penh bat virus, Powassan virus, Rio Bravo virus, Royal Farm virus, Saboya virus, Saint Louis encephalitis virus, Sal Vieja virus, San Perlita virus, Saumarer Reef virus, Sepik virus, Tembusu virus, Tick-borne encephalitis virus, Tyuleniy virus, Uganda S virus, Usutu virus, Wesselsbron virus, West Nile virus, Yaounde virus, Yellow fever virus, Yokose virus, or Zika Virus.

7. The composition according to above 5, wherein the flavivirus is dengue virus.

8. The composition according to above 5, including: at least one of tobramycin, trifluoperazine 2HCl, amikacin hydrate, hydroxychloroquine sulfate, thioridazine HCl, dihydrostreptomycin sulfate, gentamicin sulfate, netilmticin sulfate, capreomycin sulfate, paromomycin sulfate, resminostat, montelukast, norfloxacin, nedaplatin, bleomycin, nystatin, cephalothin, micafungin sodium, efavirenz and miltefosine; or at least one of pharmaceutically acceptable salts of the above compounds.

The composition of the present invention exhibits excellent effects in inhibiting the proliferation of viruses in the flavivirus genus and increasing a survival rate to infections derived from the above viruses.

DETAILED DESCRIPTION

Hereinafter, the present invention will be described in detail.

The present invention relates to a pharmaceutical composition for preventing or treating flavivirus infection.

Flavivirus is a first genus of togavirus family, and has a common antigen in this genus due to its cohesive property of erythrocytes.

As used herein, flavivirus refers to any species of virus known in the art to be included in the corresponding genus without limitation thereof, and flavivirus infection refers to a disease or virus-carrying condition caused by virus infection due to the corresponding virus.

The composition of the present invention may exhibit killing and/or growth inhibitory effects on various species of flavivirus genus. For example, the viruses may be Apoi virus, Aroa virus, Bagaza virus, Banzi virus, Bouboui virus, Bukarasa bat virus, Cacipacore virus, Carey Island virus, Cowbone Ridge virus, Dakar bat virus, dengue virus, Edge Hill virus, Entebbe bat virus, Gadgets Gully virus, Ilheus virus, Israel turkey meningoencephalomyelitis virus, Japanese encephalitis virus, Jugra virus, Jutiapa virus, Kadam virus, Kedougou virus, Kokobera virus, Koutango virus, Kyasanur Forest disease virus, Langat virus, Louping ill virus, Meaban virus, Modoc virus, Montana myotis leukoencephalitis virus, Murray Valley encephalitis virus, Ntaya virus, Omsk hemorrhagic fever virus, Phnom Penh bat virus, Powassan virus, Rio Bravo virus, Royal Farm virus, Saboya virus, Saint Louis encephalitis virus, Sal Vieja virus, San Perlita virus, Saumarez Reef virus, Sepik virus, Tembusu virus, Tick-borne encephalitis virus, Tyuleniy virus, Uganda S virus, Usutu virus, Wesselsbron virus, West Nile virus, Yaounde virus, Yellow fever virus, Yokose % virus, Zika Virus, and the like, specifically, dengue virus, and more specifically, dengue virus serotype 2, but it is not limited thereto.

The pharmaceutical composition of the present invention may include, for example, at least one of gentamicin sulfate, netilmicin, tobramycin, paromomycin, amikacin, capreomycin, trifluoperazine, dihydrostreptomycin, hydroxychloroquine, thioridazine HCl, efavirenz, miltefosine, nystatin, micafungin, bleomycin, resminostat, montelukast, norfloxacin, nedaplatin and cephalothin; or at least one of pharmaceutically acceptable salts of the above compounds.

According to one specific embodiment, the inventive composition may include at least one of gentamicin sulfate, netilmicin, tobramycin, paromomycin, amikacin, capreomycin, trifluoperazine, dihydrostreptomycin, hydroxychloroquine, thioridazine HCl, resminostat, montelukast, norfloxacin and nedaplatin; or at least one of pharmaceutically acceptable salts of the above compounds.

In addition, according to one specific embodiment, the inventive composition may include at least one of efavirenz, miltefosine, nystatin, micafungin, bleomycin and cephalothin; or at least one of pharmaceutically acceptable salts of the above compounds.

Further, according to one specific embodiment, the inventive composition may include at least one of tobramycin, trifluoperazine 2HCl, amikacin hydrate, hydroxychloroquine sulfate, thioridazine HCl, dihydrostreptomycin sulfate, gentamicin sulfate, netilmicin sulfate, capreomycin sulfate, paromomycin sulfate, resminostat, montelukast, norfloxacin, nedaplatin, bleomycin, nystatin, cephalothin, micafungin sodium, efavirenz and miltefosine; or at least one of pharmaceutically acceptable salts of the above compounds.

Pharmaceutically acceptable salts may include salts of acidic or basic groups which are possibly present in each of the above drugs (compounds). For example, the pharmaceutically acceptable salts used herein may include sodium salts, calcium salts, potassium salts, hydrochlorides, sulfates, hydrates, and the like, and may be prepared by conventional methods for preparation of salts known in the art, but it is not limited thereto.

Existing applications of each of the above drugs, inhibitory target enzymes in flavivirus as well as $IC_{50}$ may be shown in the following table, but it is not limited thereto.

TABLE 1

| Drug | Existing application | Inhibitory target enzyme | $IC_{50}$ (microM) |
|---|---|---|---|
| Gentamicin Sulfate | Antibiotics | RdRp | 2.3 |
| Netimicin | Antibiotics | RdRp | 2.9 |
| Tobramycin | Antibiotics | RdRp | 3.0 |
| Paromomycin | Antibiotics | RdRp | 4.5 |
| Amikacin | Antibiotics | RdRp | 24.3 |
| Capreomycin | Antibiotics | RdRp | 5.7 |
| Trifluoperazine | Antibiotics | RdRp | 22.1 |
| Dihydrostreptomycin | Antibiotics | RdRp | 18.4 |
| Hydroxychloroquine | Malaria medicine | RdRp | 96.0 |
| Thioridazine HCl | Anti-psychopathic medicine | RdRp | 28.1 |
| Resminostat | Anticancer agent | RdRp | 64.5 |
| Montelukast | Asthma therapeutic agent | RdRp | 38.6 |
| Norfloxacin | Anti-bacterial agent | RdRp | 26.3 |

TABLE 1-continued

| Drug | Existing application | Inhibitory target enzyme | $IC_{50}$ (microM) |
|---|---|---|---|
| Nedaplatin | Anticancer agent | RdRp | 86.4 |
| Efavirenz | HIV/AIDS (antiretroviral medication) | Helicase | 38.5 |
| Miltefosine | Antiparasitic agent (leishmaniasis) | Helicase | 17.5 |
| Nystatin | Antimycotics (polyene groups) | Helicase | 13.1 |
| Micafungin | Antifungal drug | Helicase | 5.0 |
| Bleomycin | Glycopepide Antibiotics, Anticancer agent for SCC | Helicase | 1.4 |
| Cephalothin | Cephalosporin Antibiotics (beta-lactam antibiotics) | Helicase | 26.0 |

Such substances as listed above are pre-FDA approved drugs, however, have not yet been used for flavivirus infection.

The above substances may act as an enzyme inhibitor, for example, that inhibits activity of helicase and RNA-dependent RNA polymerase (RdRp), which are enzymes required for viral replication, thereby exhibiting efficacy against flavivirus infection.

Herein, RNA-dependent RNA polymerase (RdRp) in a flavivirus genus is known to have a very high genetic preservation rate at a gene level among various RNA virus families including flavivirus, and also exhibits a high conservation rate at a protein level (polypeptide motif level) (Viruses. 2018 February; 10(2): 76.). Therefore, the pharmaceutical compositions of the present invention may exhibit efficacy against various species of the flavivirus genus.

In the case of helicases, amino acid sequences at enzyme active sites are very similarly conserved in the flavivirus, and these sequences are known to contribute to recognition of viral RNA. Further, it is known that the conserved sequences involve similar functions (contributing to hydrogen bond or hydrophobic interaction with adjacent specific sequences) in all flaviviruses and contribute to enzymatic activity. For example, the sites where dengue virus helicases and zika virus helicases are coupled to ssRNA substrates have been found to be very similar (12904-12920 Nucleic Acids Research, 2017, Vol. 45, No. 22).

The pharmaceutical composition of the present invention may be formulated while including the above substances.

The pharmaceutical compositions of the present invention may be formulated for delivery via any administration route. The "administration route" may refer to any route of administration known in the art including aerosol, nasal, oral, transmucosal, transdermal or parenteral route, or intestines, but it is not limited thereto.

The pharmaceutical composition of the present invention may also contain any pharmaceutically acceptable carrier. As used herein, the "pharmaceutically acceptable carrier" refers to pharmaceutical acceptable substances, compositions or vehicles in carrying or transporting a compound of interest from one tissue, organ or part of the body to another tissue, organ or part of the body. For example, the carrier may include liquid or solid fillers, diluents, excipients, solvents or encapsulating materials or combinations thereof. Each component of the carrier should be "pharmaceutically acceptable", i.e., compatible with the other ingredients of the formulation. The carrier should also be suitable for use when being in contact with any tissue or organ to which the carrier can contact, in particular, should not involve risks such as toxicity, irritant, allergic reactions, and/or any other complications that are too great than immunogenicity or therapeutic advantages thereof.

The composition of the present invention may be administered to a subject who tries to prevent flavivirus infection or to a subject who suffers from the flavivirus infection. The subject may be a mammal including a human, and specifically a human.

The pharmaceutical composition of the present invention may be delivered in a therapeutically effective amount. The exact therapeutically effective amount is an amount of the composition to achieve the most effective result in regard to therapeutic efficacy in a given subject. This amount may be determined in consideration of characteristics of the therapeutic compound (including activity, pharmacokinetics, pharmacodynamics and bioactivity), physiological conditions of the subject (age, sex, disease type and stage, general physical health condition, response to a given dosage and type of medicament), characteristics of the pharmaceutically acceptable carrier or carriers in the formulation, and administration routes, but it is not limited thereto. In fact, the exact therapeutically effect amount will depend upon a number of factors without limitation to the above requirements. Those skilled in the art in the clinical and pharmacological arts will determine the therapeutically effective amount through routine experimentation, for example, by monitoring the subject's response to administration of the compound and adjusting the dosage accordingly.

The present invention also relates to a composition for inhibiting growth of flavivirus or killing the same.

The composition of the present invention may include at least one of gentamicin sulfate, netilmicin, tobramycin, paromomycin, amikacin, capreomycin, trifluoperazine, dihydrostreptomycin, hydroxychloroquine, thioridazine HCl, efavirenz, miltefosine, nystatin, micafungin, bleomycin, resminostat, montelukast, norfloxacin, nedaplatin and cephalothin; or at least one of pharmaceutically acceptable salts of the above compounds.

According to one specific embodiment, the inventive composition may include at least one of gentamicin sulfate, netilmicin, tobramycin, paromomycin, amikacin, capreomycin, trifluoperazine, dihydrostreptomycin, hydroxychloroquine, thioridazine HCl, resminostat, montelukast, norfloxacin and nedaplatin; or at least one of pharmaceutically acceptable salts of the above compounds.

In addition, according to one specific embodiment, the inventive composition may include at least one of efavirenz, miltefosine, nystatin, micafungin, bleomycin and cephalothin; or at least one of pharmaceutically acceptable salts of the above compounds.

Further, according to one specific embodiment, the inventive composition may include at least one of tobramycin, trifluoperazine 2HCl, amikacin hydrate, hydroxychloroquine sulfate, thioridazine HCl, dihydrostreptomycin sulfate, gentamicin sulfate, netilmicin sulfate, capreomycin sulfate, paromomycin sulfate, resminostat, montelukast, norfloxacin, nedaplatin, bleomycin, nystatin, cephalothin, micafungin sodium, efavirenz and miltefosine; or at least one of pharmaceutically acceptable salts of the above compounds.

The composition of the present invention may exhibit killing and/or growth inhibitory effects on various species of flavivirus genus. For example, the viruses may be Apoi virus, Aroa virus, Bagaza virus, Banzi virus, Bouboui virus, Bukarasa bat virus, Cacipacore virus, Carey Island virus, Cowbone Ridge virus, Dakar bat virus, dengue virus, Edge Hill virus, Entebbe bat virus, Gadgets Gully virus, Ilheus virus, Israel turkey meningoencephalomyelitis virus, Japanese encephalitis virus, Jugra virus, Jutiapa virus, Kadam virus, Kedougou virus, Kokobera virus, Koutango virus, Kyasanur Forest disease virus, Langat virus, Louping ill virus, Meaban virus, Modoc virus, Montana myotis leukoencephalitis virus, Murray Valley encephalitis virus, Ntaya virus, Omsk hemorrhagic fever virus, Phnom Penh bat virus, Powassan virus, Rio Bravo virus, Royal Farm virus, Saboya virus, Saint Louis encephalitis virus, Sal Vieja virus, San Perlita virus, Saumare: Reef virus, Sepik virus, Tembusu virus, Tick-borne encephalitis virus, Tyuleniy virus, Uganda S virus, Usutu virus, Wesselsbron virus, West Nile virus, Yaounde virus, Yellow fever vrirus, Yokose virus, Zika Virus, and the like, specifically, dengue virus, and more specifically, dengue virus serotype 2, but it is not limited thereto.

The composition of the present invention may be formulated as the pharmaceutical composition exemplified above, but it is not limited thereto.

In addition, the present invention also relates to a use for preparation of a composition for preventing or treating flavivirus infection including at least one of gentamicin sulfate, netilmicin, tobramycin, paromomycin, amikacin, capreomycin, trifluoperazine, dihydrostreptomycin, hydroxychloroquine, thioridazine HCl, efavirenz, miltefosine, nystatin, micafungin, bleomycin, resminostat, montelukast, norfloxacin, nedaplatin and cephalothin; or at least one of pharmaceutically acceptable salts of the above compounds.

According to one specific embodiment, the inventive composition may include at least one of gentamicin sulfate, netilmicin, tobramycin, paromomycin, amikacin, capreomycin, trifluoperazine, dihydrostreptomycin, hydroxychloroquine, thioridazine HCl, resminostat, montelukast, norfloxacin and nedaplatin; or at least one of pharmaceutically acceptable salts of the above compounds.

In addition, according to one specific embodiment, the inventive composition may include at least one of efavirenz, miltefosine, nystatin, micafungin, bleomycin and cephalothin; or at least one of pharmaceutically acceptable salts of the above compounds.

Further, according to one specific embodiment, the inventive composition may include at least one of tobramycin, trifluoperazine 2HCl, amikacin hydrate, hydroxychlozoquine sulfate, thioridazine HCl, dihydrostreptomycin sulfate, gentamicin sulfate, netilmicin sulfate, capreomycin sulfate, paromomycin sulfate, resminostat, montelukast, norfloxacin, nedaplatin, bleomycin, nystatin, cephalothin, micafungin sodium, efavirenz and miltefosine; or at least one of pharmaceutically acceptable salts of the above compounds.

Flavivirus infections in the use of the present invention may be caused by the above-described viruses.

As described above, the compounds (drugs) or pharmaceutically acceptable salts thereof may exhibit excellent effects of inhibiting growth of flavivirus growth and killing the same, and thus may be used in the preparation of a composition for preventing or treating flavivirus infection.

Further, the present invention also relates to a method for preventing or treating flavivirus infection by administering, to a subject, at least one of gentamicin sulfate, netilmicin, tobramycin, paromomycin, amikacin, capreomycin, trifluoperazine, dihydrostreptomycin, hydroxychloroquine, thioridazine HCl, efavirenz, miltefosine, nystatin, micafungin, bleomycin, resminostat, montelukast, norfloxacin, nedaplatin and cephalothin; or at least one of pharmaceutically acceptable salts of the above compounds.

According to one specific embodiment, the inventive composition may include at least one of gentamicin sulfate, netilmicin, tobramycin, paromomycin, amikacin, capreomycin, trifluoperazine, dihydrostreptomycin, hydroxychloroquine, thioridazine HCl, resminostat, montelukast, norfloxacin and nedaplatin; or at least one of pharmaceutically acceptable salts of the above compounds.

In addition, according to one specific embodiment, the inventive composition may include at least one of efavirenz, miltefosine, nystatin, micafungin, bleomycin and cephalothin; or at least one of pharmaceutically acceptable salts of the above compounds.

Further, according to one specific embodiment, the inventive composition may include at least one of tobramycin, trifluoperazine 2HCl, amikacin hydrate, hydroxychloroquine sulfate, thioridazine HCl, dihydrostreptomycin sulfate, gentamicin sulfate, netilmicin sulfate, capreomycin sulfate, paromomycin sulfate, resminostat, montelukast, norfloxacin, nedaplatin, bleomycin, nystatin, cephalothin, micafungin sodium, efavirenz and miltefosine; or at least one of pharmaceutically acceptable salts of the above compounds.

The subject may be any subject who is potentially infected with the flavivirus infection, and specifically, may be a mammal including a human, and more specifically, a human, but it is not limited thereto.

Flavivirus infections may be caused by the viruses described above.

Hereinafter, the present invention will be described in detail with reference to Examples.

Example

1. Procedure
(1) Evaluation of Call Survival Rate

CCK-8 analysis was performed according to the manufacturer's instructions.

Prior to the experiment, VeroE6 cells were seeded at densities of $10.5 \times 10^4$ cells/cm$^2$ and $7.0 \times 10^4$ cells/cm$^2$, respectively. After 24 hours of incubation at 37° C., 5. CO$_2$, montelukast was treated at a continuously diluted concentration for 48 hours. Each group was treated with CCK-8 reagents at a concentration of 10?v/v and incubated for 1-4 hours in normal cell culture conditions. Quantitative analysis of changes in colorimetric intensity was performed by measuring an optical density of formazan salt at 450 nm using a microplate reader (Molecular Devices, Inc., USA). The experiment was performed in triplicate with data represented as mean t SEM.

(2) Experimental Group of Intracellular Virus Infection Experiment

Prior to the experiment, VeroE6 cells were seeded at densities of $10.5 \times 10^4$ cells/cm$^2$, and $7.0 \times 10^4$ cells/cm$^2$, respectively. After 24 hours of incubation at 37° C., 54 CO$_2$, dengue virus serotype 2 was inoculated in each cell culture with MOI of 0.1, 0.5 and 2.5, respectively, in a serum-free medium for 2 hours. The culture plate was shaken gently every 30 minutes to evenly distribute the virus in the cells. Montelukast solutions were prepared at serially diluted concentrations in each complete culture medium containing 0.75, methyl cellulose. After incubation, the virus medium was removed and cells were washed once with sterilized PBS, and then treated with a compound solution. The cells were incubated for 48 hours in the culture chamber. After incubation, each group was prepared for focal formation assay (FFA) and relative viral RNA expression analysis. For FFA, the compound solution was removed and the cells were washed once with sterilized PBS, and then fixed with 4% paraform aldehyde. The cells were washed with TRIZOL for viral RNA expression analysis and stored at −70° C. for further analysis.

(3) Focal Formation Analysis (FFA)

FFA was performed on NS1 protein of dengue virus (DV) serotype 2. Cells fixed with 43 paraformaldehyde were washed three times with PBS. A blocking solution was treated for 1 hour at room temperature. After washing with PBS, each group was treated with a primary antibody (Mouse anti-Flavivirus NS1, 1: 2000) for 2 hours at room temperature or overnight at 4° C. After washing with PBS, a secondary antibody (anti-mouse IgG-FITC, 1: 500) was applied to each group for 1 hour at room temperature. After rinsing, each group was treated with PBS containing 10 μg/ml HOECHST 33342 for nuclear staining. Viral focus-forming units stained with fluorescence were observed and analyzed under a microscope (Olympus, Japan).

(4) Animal Experiment

AG129 mice (129/Sv IFN-α/β, -γ receptor deficiency) were purchased from Marshall BioResources (Aldbrough, UK). All experimental procedures were pre-approved by Jeonbuk National University IACUC, and were performed in accordance with guidelines for evaluation and recommendations of the Korean Association for Laboratory Animal Research. In order to avoid unexpected contact and contamination as DV was transferred by mosquitoes, cages with filter covers were used.

(5) Experimental Group for In Vivo Virus Infection Experiment

In order to determine an appropriate viral titer for infection, AG129 mice (10-12 weeks) were inoculated by intraperitoneal injection of various viral titers of $10^6$, $5 \times 10^6$ and $10^7$ FFU. In order to assess antivirality of montelukast, AG129 mice (10-12 weeks) were injected with $10^7$ FFU (IP) and then 200 μl of montelukast (IP, 10 mg/kg/day) or PBS. Medication was performed once a day. A negative control (uninfected group) was subjected to administration of 300 μl of PBS (IP) instead of virus. For a drug control group, 200 μl of montelukast (IP, 10 mg/kg/day) was administered alone to uninfected AG129 mice.

(6) Mouse Weight Lose and Survival Rate Analysis

Weight loss and mortality status were monitored daily. In the survival analysis, euthanized mice showing severe disease-related symptoms or rapid weight loss were recorded as current deaths after exhibition. Each body weight was analyzed as a relative percentage to 0 day.

(7) Viremia Analysis, Whole Blood RMA Expression Analysis

On day 3, blood was collected from each mouse and transferred to an EDTA coated anticoagulant tube. After shaking for 10 minutes and gently mixing, 20 µl of each sample was analyzed by whole blood count using HEMAVET 950FS (Drew Scientific). The measured value of each factor was semi-quantified relative to that of the uninfected control. Plasma was isolated by centrifugation at 8000 g and 4° C. for 15 minutes in order to analyze cytokine hyperemia and expression changes. Plasma virus titer (viremia) and viral RNA expression in whole blood were analyzed by quantitative real-time PCR (qRT-PCR).

All samples were analyzed according to manufacturer's instructions (BD Biosciences, USA).

(8) Mouse Necropsy

On day 3, mice were sacrificed from each group (n=6). Organ samples (spleen, liver, lung, small intestine and large intestine) were collected and prepared for viral RNA expression analysis and histopathology analysis. The spleen was weighed to measure splenomegaly. Half of the spleen, liver and lung were homogenized for viral RNA expression analysis and treated with TRIZOL reagent, then stored at −70° C. for further analysis. The same procedure was applied to the entire samples of the small and large intestines. The other half of the spleen, liver and lung were soaked in 4% paraformaldehyde for fixation and stored at 4° C.

(9) Relative Viral RNA Expression Level Analysis

In order to investigate viral RNA expression changes in the collected samples, RNA was isolated from cell-based and animal-based samples treated with TRIZOL reagents, followed by cDNA synthesis using MLVRT™ reverse transcriptase according to the instructions.

For target gene amplification, each primer was designed taking into account overlap between two exons of the target gene having a GC content of less than 50% and an expected amplicon size of about 100 bps. Primer sequences were identified as shown in Table 2. For quantification of viral RNA, quantitative real time PCR (qRT-PCR) was performed. Each reaction was performed in 20 µL volume using SYBR green master mix. Quantstudio 3™ (Applied Biosystems Inc., USA) was used for the present study in two-stage amplification process. For analysis of viremia, a linear correlation standard curve was established between the viral titer (FFU/mL) and the corresponding threshold cycle (CT) value.

Virus in plasma was calculated according to an equation of standard curve. The standard curve was induced for serially diluted virus titers. For cell-based group and mouse organ samples (including whole blood), semi-quantitative viral RNA was analyzed for GAPDH as an endogenous control.

(10) Pathology Analysis

Organ samples fixed with 4% paraformaldehyde were subjected to a series of procedures such as paraffin insertion, sectioning and staining with hematoxylin and eosin.

(11) Statistical Analysis

Data plots using concentration dependent analysis were analyzed with OriginPro 8. Briefly, a log S curve was used for each data set. Error bars represent ±SEM unless otherwise indicated. Statistical significance of in vitro and in vivo antiviral efficacy assays was assessed by a two-tailed t-test. The statistical significance of the survival rate was analyzed by a log-rank test of R (R Foundation for Statistical Computing, Austria).

2. Result (1) Confirmation of Dengue Virus Enzyme Activity Inhibition

Figure 1:
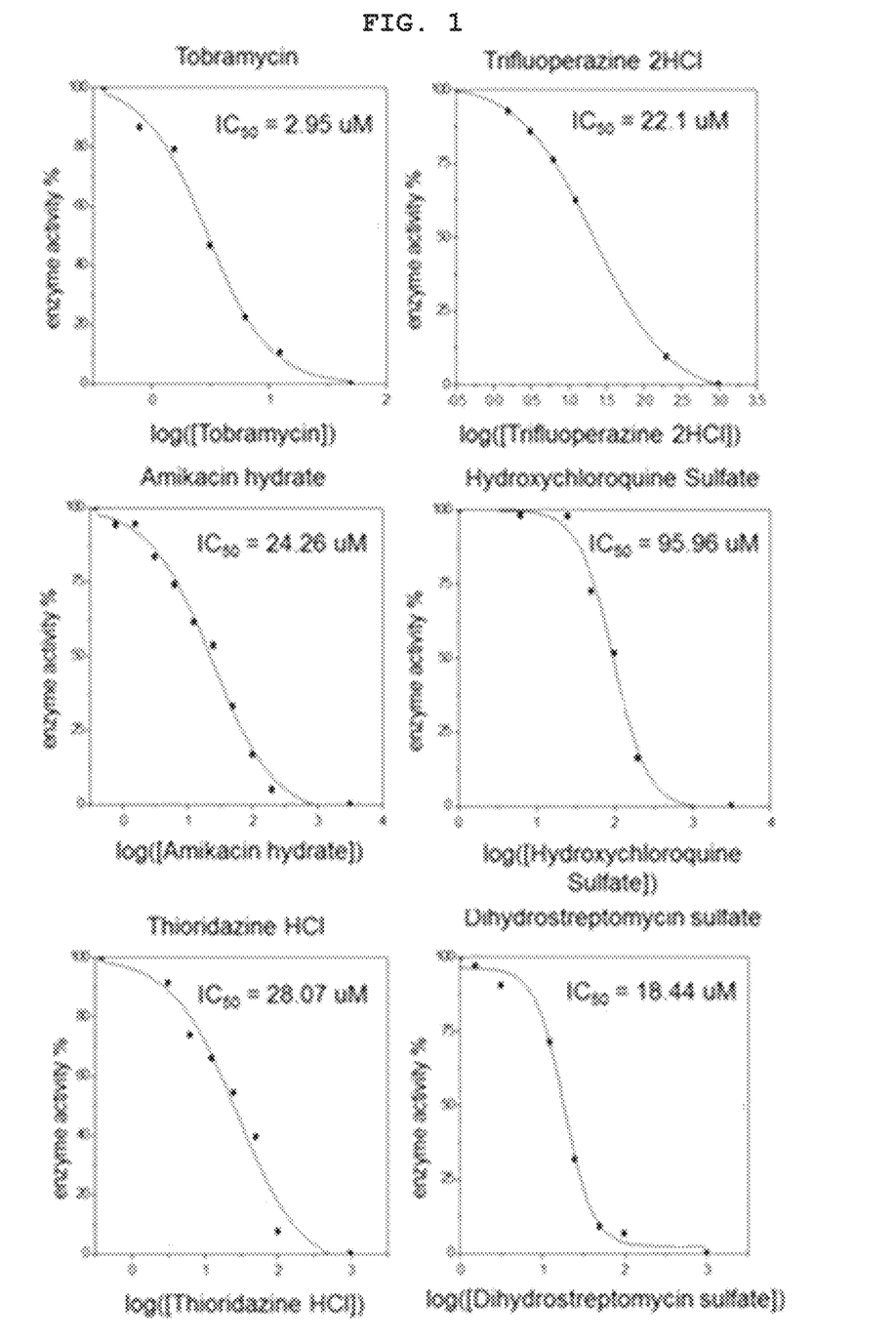
FIGS. 1 to 3 are graphs illustrating dengue virus RdRp activity inhibitory effects.
Figure 2:
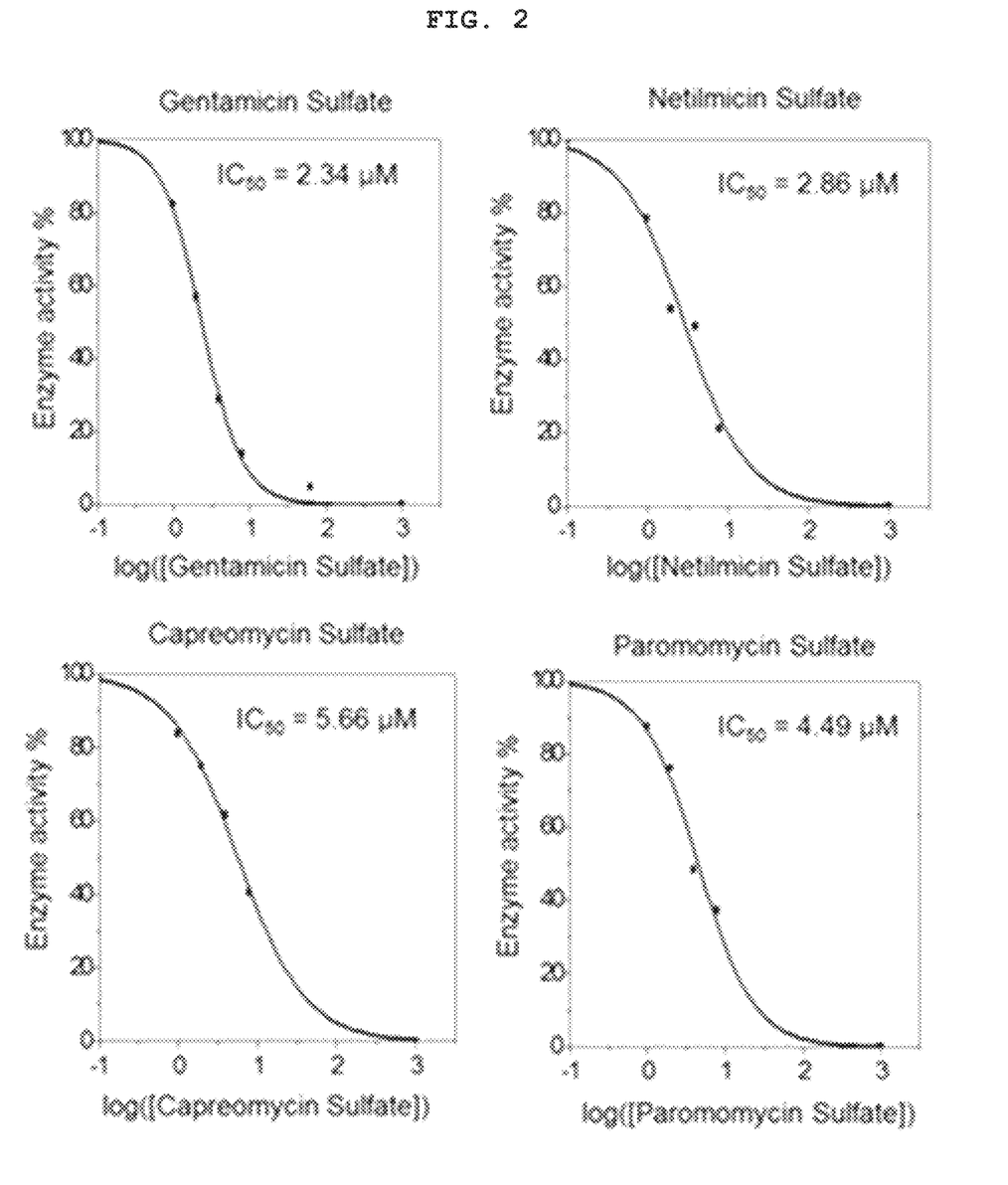
Figure 3:
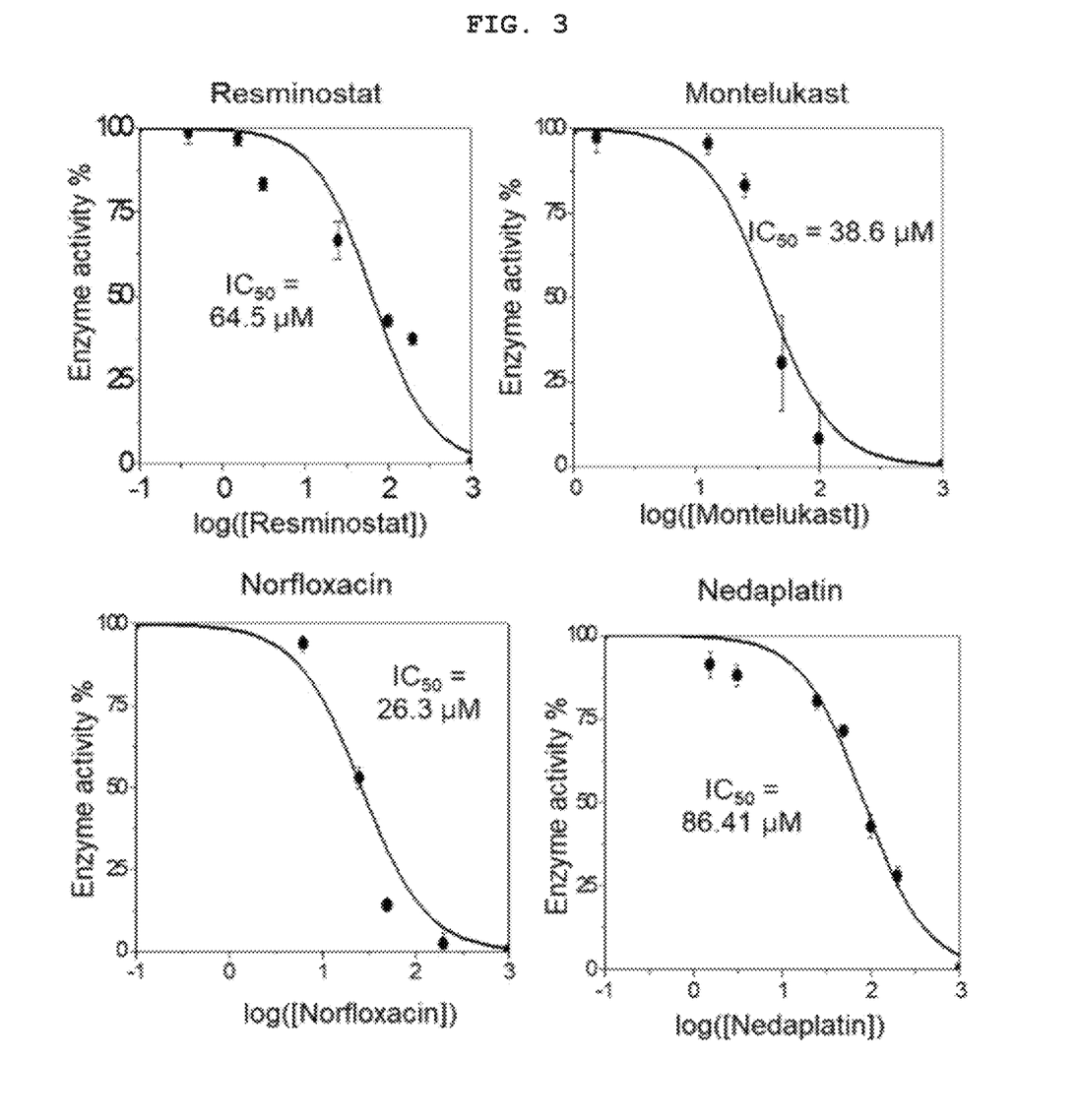

A degree of inhibition of dengue virus RdRp enzyme activity depending on the concentrations of 14 compounds was determined ($IC_{50}$ values presented, FIGS. 1 to 3).

Referring to FIGS. 1 to 3, it can be seen that 14 compounds inhibit dengue virus RdRp with high efficiency.

(2) Confirmation of Inhibition of Helicase Enzyme Activity

Figure 4:
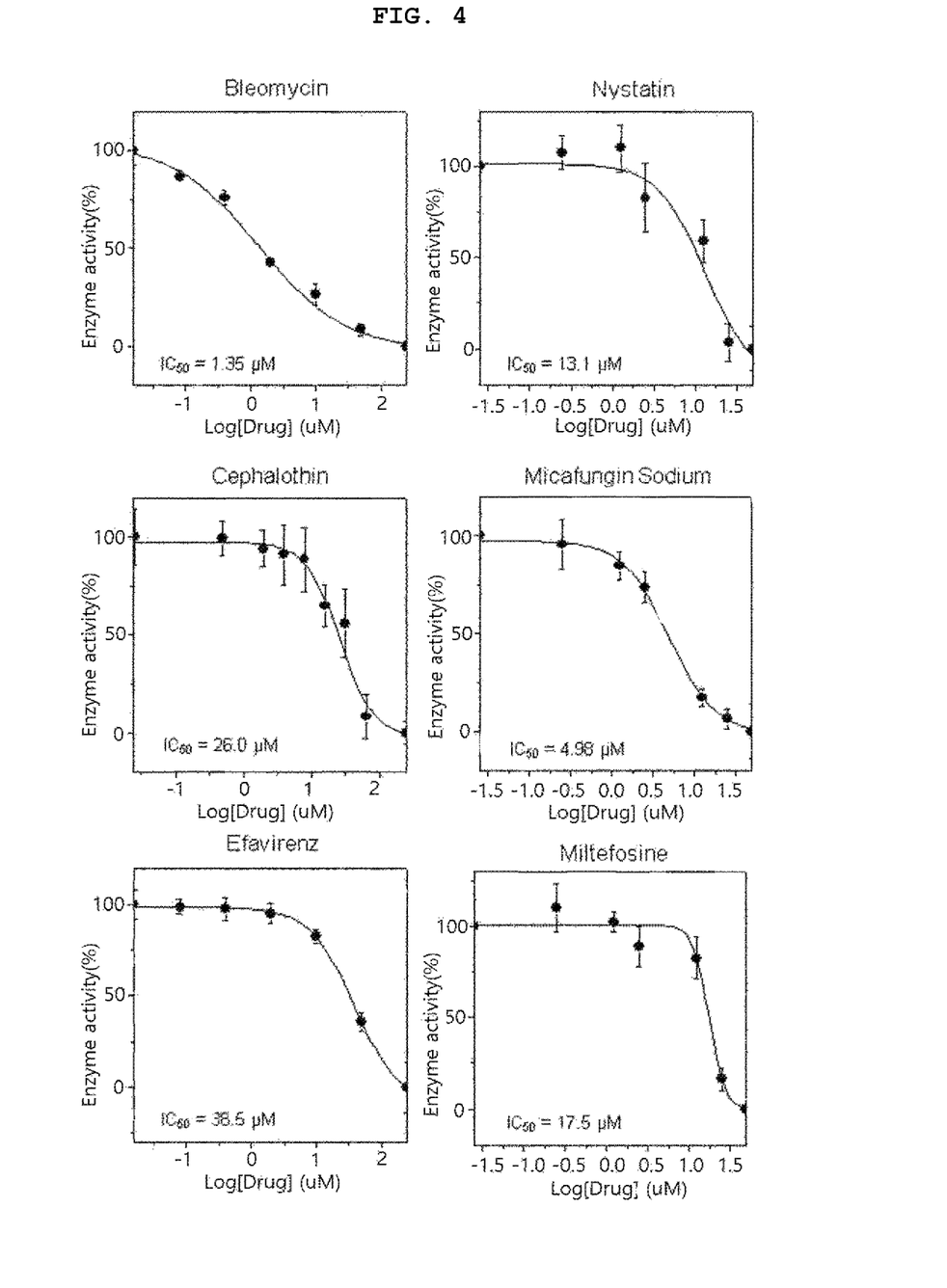
FIG. 4 is graphs illustrating dengue virus helicase activity inhibitory effects.

A degree of inhibition of dengue virus helicase activity depending on the concentrations of 6 compounds was confirmed ($IC_{50}$ values presented, FIG. 4).

Referring to FIG. 4, it can be seen that 6 types of compounds inhibit dengue virus helicase with high efficiency.

(3) Confirmation of Dengue Viremia Reduction Effect

Figure 5:
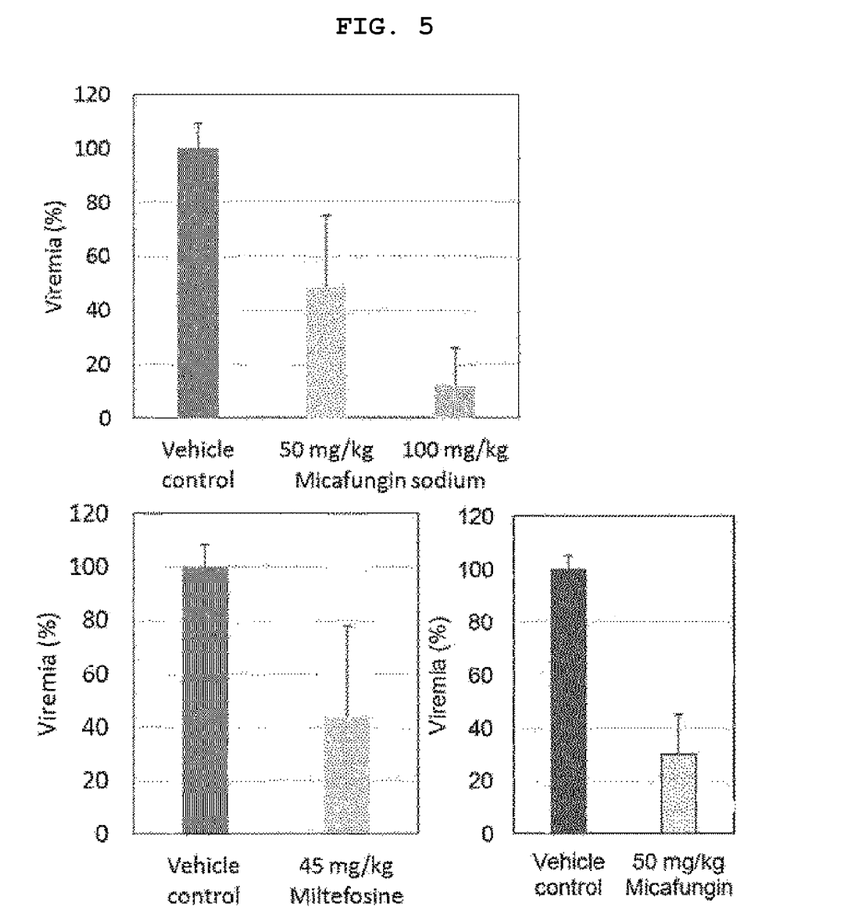
FIG. 5 is graphs illustrating dengue viremia reduction effects.

A dengue infection model (AG129 mouse) was used to confirm DENV viremia reduction in mouse blood after drug treatment (FIG. 5). Micafungin sodium was introduced with intraperitoneal (IP) injection, miltefosine was introduced with oral injection, and a vehicle control was introduced with PBS.

Referring to FIG. 5, it can be seen that the dengue viremia is significantly reduced by micafungin sodium and/or miltefosine treatment.

(4) Confirmation of Dengue Virus Reduction Effect

Cell-based evaluation was performed to evaluate anti-dengue virus activity of each compound. In vitro viral focal formation assays were performed to investigate concentration dependent antiviral effects of each compound using VeroE6 cells. Virus focus images are shown in FIG. 6.

Figure 6:
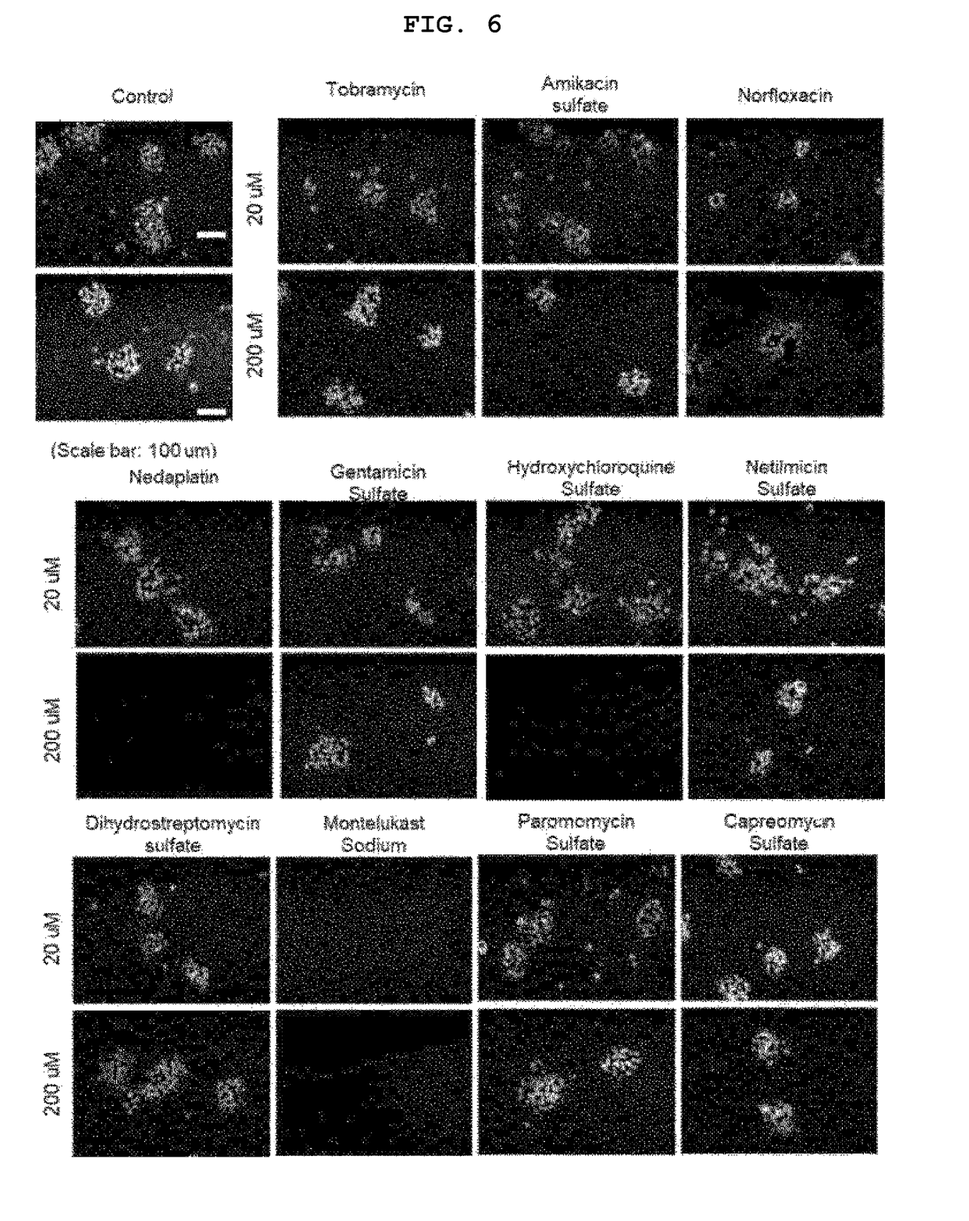
FIG. 6 is images illustrating FFA results showing dengue virus reduction effects.

Referring to FIG. 6, it can be seen that the virus is significantly reduced during treatment of 11 types of compounds.

Figure 7:
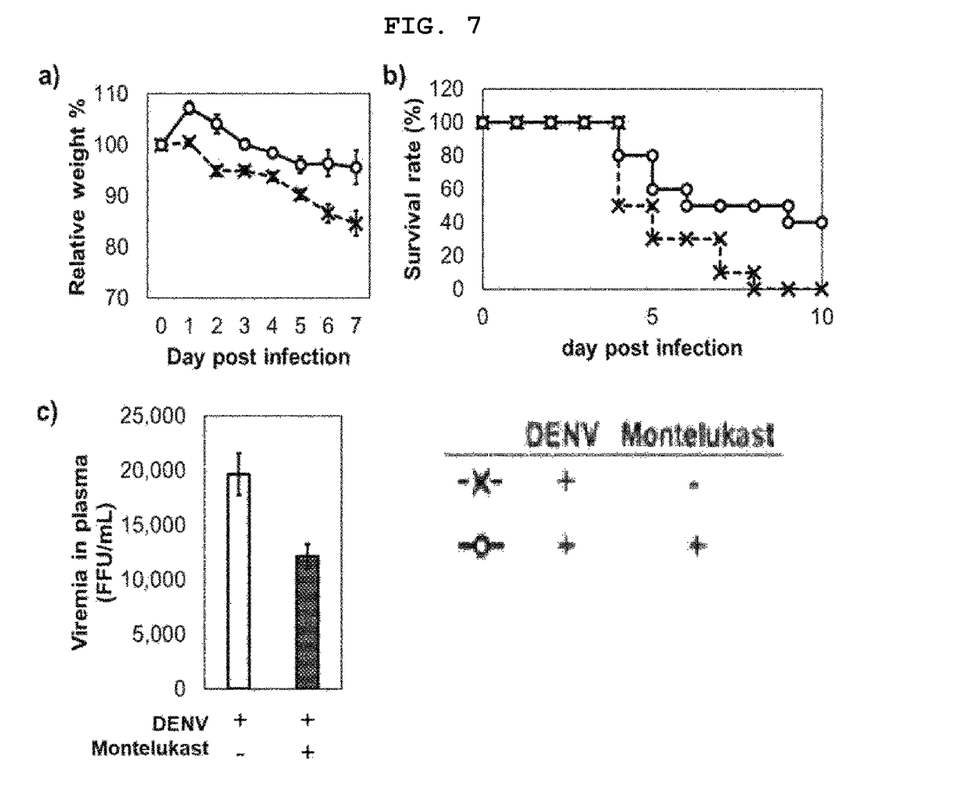
FIG. 7 is graphs illustrating dengue virus growth inhibitory effects and increase in a survival rate to infection.

(5) Confirmation of Virus Growth Inhibitory Effect and Increase in Survival Rate DENV2 (dengue virus serotype 2) infected AG129 mice (10-12 weeks, n=10) were treated with 10 mg/kg of montelukast once daily. As a vehicle, PBS was injected. After infection, body weights were measured by date, and the

TABLE 2

| Gene | Forward primer | Reverse primer | Amplicon size (bp) |
| --- | --- | --- | --- |
| Human GAPDH | TCACTGCCACCCAGAAGACTG (SEQ ID NO: 1) | GGATGACCTTGCCCACAGC (SEQ ID NO: 2) | 123 |
| Mouse GAPDH | TGACCTCAACTACATGGTCTACA (SEQ ID NO: 3) | CTTCCCATTCTCGGCCTTG (SEQ ID NO: 4) | 85 |
| DV2 NS1 | GCTCCTTCAATGACAATGCGCTGTA (SEQ ID NO: 5) | CCTGAAACCCCTTCCACGAAGTC (SEQ ID NO: 6) | 65 | survival rate and hyperemia in plasma were measured on day three after infection (FIG. 7).

Referring to FIG. 7, it can be seen that the montelukast-administered group has a low degree of weight loss, a high survival rate and a low hyperemia.

(6) Confirmation of Tissue-Specific Antiviral Effect

Tissue-specific antiviral effects of montelukast have been identified for each major organ.

DENV2 (dengue virus serotype 2) infected AG129 mice (n=6) were treated with 10 mg/kg montelukast daily. Mice were sacrificed on day three after treatment. Then, whole blood, spleen, liver, lung, small intestine and large intestine were collected, and half of the spleen, liver and lung were preserved in paraformaldehyde. The other half was subjected to RNA isolation and virus titer analysis.

Figure 8:
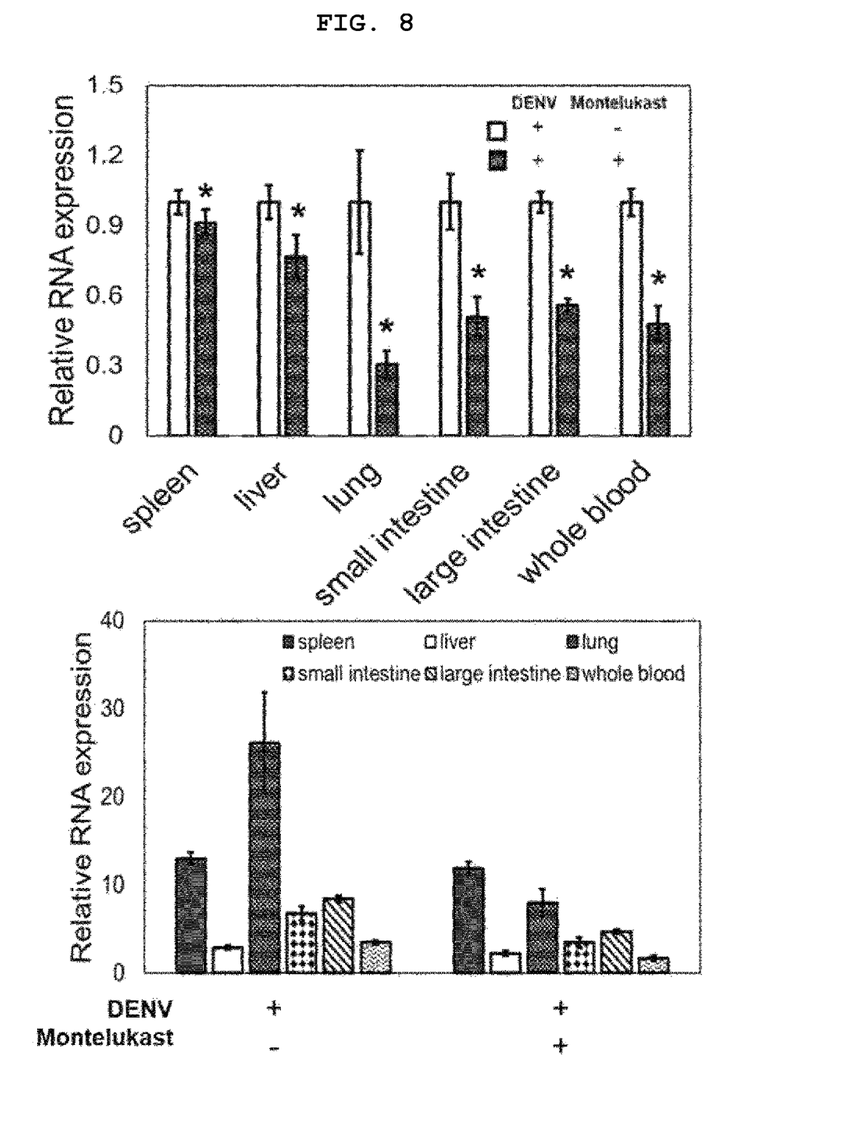
FIG. 8 is graphs illustrating tissue-specific anti-dengue virus effects.

Relative dengue virus RNA expression was measured from each tissue sample, results thereof are shown in FIG. 8.

Referring to FIG. 8, it can be seen that the dengue virus RNA expression is significantly low in the montelukast treatment group.

(7) Histological Analysis of Virus Proliferation Inhibitory Effect

Dengue virus infected mice were treated with montelukast to obtain histological data of the treated group and untreated group. After resection of the spleen and liver of each group, H & E staining was performed. Results thereof are shown in FIG. 9.

Figure 9:
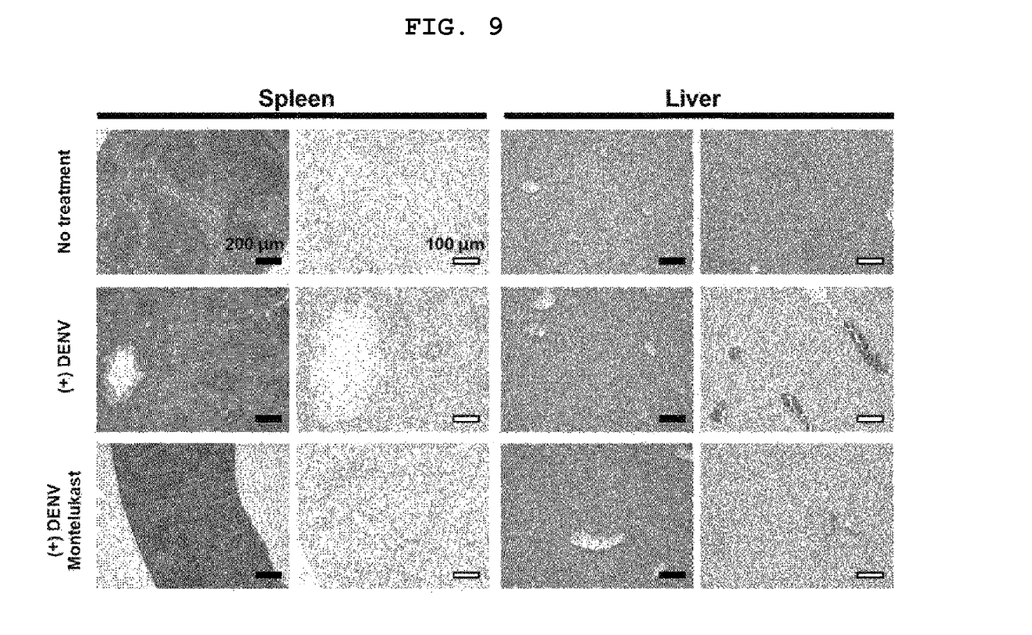
FIG. 9 is images illustrating confirmation of virus growth inhibitory effects by histological analysis.

Referring to FIG. 9, it can be seen that virus replication is reduced by the montelukast treatment.

A sequence listing electronically submitted with the present application on Oct. 27, 2020 as an ASCII text file named 20201027_Q38520LC32_TU_SEQ, created on Oct. 23, 2020 and having a size of 2000 bytes, is incorporated herein by reference in its entirety.

The invention claimed is:

1. A method for treating a flavivirus infection, the method comprising administering to a subject in need thereof a composition comprising:

at least one of paromomycin, capreomycin, thioridazine HCl, miltefosine, resminostat, nedaplatin and cephalothin; or at least one of pharmaceutically acceptable salts of the above compounds.

2. The method of claim 1, wherein the flavivirus infection is an infection derived from at least one selected from the group consisting of Apoi virus, Aroa virus, Bagaza virus, Banzi virus, Bouboui virus, Bukarasa bat virus, Cacipacore virus, Carey Island virus, Cowbone Ridge virus, Dakar bat virus, dengue virus, Edge Hill virus, Entebbe bat virus, Gadgets Gully virus, Ilheus virus, Israel turkey meningoencephalomyelitis virus, Japanese encephalitis virus, Jugra virus, Jutiapa virus, Kadam virus, Kedougou virus, Kokobera virus, Koutango virus, Kyasanur Forest disease virus, Langat virus, Louping ill virus, Meaban virus, Modoc virus, Montana myotis leukoencephalitis virus, Murray Valley encephalitis virus, Ntaya virus, Omsk hemorrhagic fever virus, Phnom Penh bat virus, Powassan virus, Rio Bravo virus, Royal Farm virus, Saboya virus, Saint Louis encephalitis virus, Sal Vieja virus, San Perlita virus, Saumarez Reef virus, Sepik virus, Tembusu virus, Tick-borne encephalitis virus, Tyuleniy virus, Uganda S virus, Usutu virus, Wesselsbron virus, West Nile virus, Yaounde virus, Yellow fever virus, Yokose virus, Zika Virus and a combination thereof.

3. The method of claim 1, wherein the flavivirus infection is a dengue virus-derived infection.

4. The method of claim 1, wherein the composition further comprises at least one of tobramycin, trifluoperazine 2HCl, amikacin hydrate, thioridazine HCl, dihydrostreptomycin sulfate, gentamicin sulfate, netilmicin sulfate, capreomycin sulfate, paromomycin sulfate, resminostat, norfloxacin, nedaplatin, bleomycin, nystatin, cephalothin, micafungin sodium, efavirenz and miltefosine; or at least one of pharmaceutically acceptable salts of the above compounds.

5. A method for inhibiting growth of flavivirus or killing the same, the method comprising administering to a subject in need thereof a composition comprising:

at least one of paromomycin, capreomycin, thioridazine HCl, miltefosine, resminostat, nedaplatin and cephalothin; and at least one of pharmaceutically acceptable salts of the above compounds.

6. The method of claim 5, wherein the flavivirus is Apoi virus, Aroa virus, Bagaza virus, Banzi virus, Bouboui virus, Bukarasa bat virus, Cacipacore virus, Carey Island virus, Cowbone Ridge virus, Dakar bat virus, dengue virus, Edge Hill virus, Entebbe bat virus, Gadgets Gully virus, Ilheus virus, Israel turkey meningoencephalomyelitis virus, Japanese encephalitis virus, Jugra virus, Jutiapa virus, Kadam virus, Kedougou virus, Kokobera virus, Koutango virus, Kyasanur Forest disease virus, Langat virus, Louping ill virus, Meaban virus, Modoc virus, Montana myotis leukoencephalitis virus, Murray Valley encephalitis virus, Ntaya virus, Omsk hemorrhagic fever virus, Phnom Penh bat virus, Powassan virus, Rio Bravo virus, Royal Farm virus, Saboya virus, Saint Louis encephalitis virus, Sal Vieja virus, San Perlita virus, Saumarez Reef virus, Sepik virus, Tembusu virus, Tick-borne encephalitis virus, Tyuleniy virus, Uganda S virus, Usutu virus, Wesselsbron virus, West Nile virus, Yaounde virus, Yellow fever virus, Yokose virus, or Zika Virus.

7. The method of claim 5, wherein the flavivirus is dengue virus.

8. The method of claim 5, wherein the composition comprises at least one of tobramycin, trifluoperazine 2HCl, amikacin hydrate, thioridazine HCl, dihydrostreptomycin sulfate, gentamicin sulfate, netilmicin sulfate, capreomycin sulfate, paromomycin sulfate, resminostat, norfloxacin, nedaplatin, bleomycin, nystatin, cephalothin, micafungin sodium, efavirenz and miltefosine; or at least one of pharmaceutically acceptable salts of the above compounds.

9. The method of claim 5, wherein the composition comprises paromomycin.

10. The method of claim 5, wherein the composition comprises capreomycin.

11. The method of claim 5, wherein the composition comprises thioridazine HCl.

12. The method of claim 5, wherein the composition comprises miltefosine.

13. The method of claim 5, wherein the composition comprises resminostat.

14. The method of claim 5, wherein the composition comprises nedaplatin.

15. The method of claim 5, wherein the composition comprises cephalothin.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Human GAPDH Forward primer

<400> SEQUENCE: 1
tcactgccac ccagaagact g                                      21

<210> SEQ ID NO 2
<211> LENGTH: 19
<212> TYPE: DNA
<213> ORGANISM: Artificial Sequence
<220> FEATURE:
<223> OTHER INFORMATION: Human GAPDH Reverse primer

<400> SEQUENCE: 2
ggatgacctt gcccacagc                                         19

<210> SEQ ID NO 3
<211> LENGTH: 23
<212> TYPE: DNA
<213> ORGANISM: Artificial Sequence
<220> FEATURE:
<223> OTHER INFORMATION: Mouse GAPDH Forward primer

<400> SEQUENCE: 3
tgacctcaac tacatggtct aca                                    23

<210> SEQ ID NO 4
<211> LENGTH: 19
<212> TYPE: DNA
<213> ORGANISM: Artificial Sequence
<220> FEATURE:
<223> OTHER INFORMATION: Mouse GAPDH Reverse primer

<400> SEQUENCE: 4
cttcccattc tcggccttg                                         19

<210> SEQ ID NO 5
<211> LENGTH: 25
<212> TYPE: DNA
<213> ORGANISM: Artificial Sequence
<220> FEATURE:
```

```
<223> OTHER INFORMATION: DV2 NS1 Forward primer

<400> SEQUENCE: 5
gctccttcaa tgacaatgcg ctgta                                          25

<210> SEQ ID NO 6
<211> LENGTH: 23
<212> TYPE: DNA
<213> ORGANISM: Artificial Sequence
<220> FEATURE:
<223> OTHER INFORMATION: DV2 NS1 Reverse primer

<400> SEQUENCE: 6
cctgaaaccc cttccacgaa gtc                                            23
```